(12) United States Patent
Becker

(10) Patent No.: US 7,108,714 B1
(45) Date of Patent: Sep. 19, 2006

(54) EXPANDABLE INTRALUMINAL ENDOPROSTHESIS

(75) Inventor: Gary J. Becker, Miami, FL (US)

(73) Assignee: Orbus Medical Technologies, Inc., Fort Lauderdale, FL (US)

( * ) Notice: Subject to any disclaimer, the term of this patent is extended or adjusted under 35 U.S.C. 154(b) by 0 days.

(21) Appl. No.: 09/511,481

(22) Filed: Feb. 23, 2000

Related U.S. Application Data

(63) Continuation of application No. 09/094,402, filed on Jun. 10, 1998, now Pat. No. 6,117,165.

(30) Foreign Application Priority Data

| Jun. 13, 1997 | (EP) | ................................ 97201799 |
| May 6, 1998 | (EP) | ................................ 98201446 |

(51) Int. Cl.
*A61F 2/06* (2006.01)

(52) U.S. Cl. .................... 623/1.15; 623/1.17; 623/1.22

(58) Field of Classification Search .................... 623/1, 623/11, 12, 1.17, 1.22; 606/191, 198, 192, 606/194, 195
See application file for complete search history.

(56) References Cited

U.S. PATENT DOCUMENTS

| 5,133,732 A | * | 7/1992 | Wiktor ........................ 606/195 |
| 5,217,483 A | * | 6/1993 | Tower ......................... 606/198 |
| 5,226,913 A | * | 7/1993 | Pinchuk .......................... 623/1 |
| 5,304,200 A | * | 4/1994 | Spaulding .................... 606/198 |
| 5,449,373 A |   | 9/1995 | Pinchasik et al. |
| 5,507,767 A | * | 4/1996 | Maeda et al. ................. 623/1.2 |
| 5,716,396 A | * | 2/1998 | Williams, Jr. ............... 623/1.22 |
| 5,725,572 A | * | 3/1998 | Lam et al. ....................... 623/1 |
| 5,733,303 A | * | 3/1998 | Israel et al. ................. 623/1.15 |
| 5,776,161 A | * | 7/1998 | Globerman .................. 606/194 |
| 5,824,043 A | * | 10/1998 | Cottone, Jr. .................... 623/1 |
| 5,843,164 A | * | 12/1998 | Frantzen et al. ................ 623/1 |
| 5,913,897 A | * | 6/1999 | Corso et al. ................. 623/1.15 |
| 5,925,061 A | * | 7/1999 | Ogi et al. ..................... 623/1.2 |
| 6,013,854 A | * | 1/2000 | Moriuchi .................... 623/1.11 |
| 6,203,569 B1 | * | 3/2001 | Wijay ........................ 623/1.15 |

FOREIGN PATENT DOCUMENTS

| EP | 0565251 A1 | 10/1993 |
| EP | 0645125 A1 | 3/1995 |
| EP | 0801934 A2 | 10/1997 |
| GB | 2281865 A | 3/1995 |
| WO | WO 96 26689 | 9/1996 |
| WO | WO 97 21399 | 6/1997 |
| WO | WO 97 40780 | 11/1997 |

* cited by examiner

*Primary Examiner*—David J. Isabella
*Assistant Examiner*—Urmi Chattopadhyay
(74) *Attorney, Agent, or Firm*—White & Case LLP

(57) ABSTRACT

An expandable intraluminal endoprosthesis including a tubular member (1) a first diameter which permits intraluminal delivery of the member into a lumen of a body passageway, particularly a blood vessel. The tubular member (1) is capable of acquiring a second, expanded and deformed diameter upon the application from the interior of the tubular member of a radially outwardly extending force, which second diameter is variable and dependent on the amount of the force applied to the tubular member. Such a tubular member may be expanded and deformed to expand the lumen of the body passageway. The wall of the tubular member includes a substantially continuous structure (2) of mutually staggered undulations. This structure has been separated from a tube wall and exhibits at least one pattern which advances substantially helically along a longitudinal axis of the tubular member. Connection elements within the structure connect adjacent undulations to each other. These connection elements are an integral extension of the undulations thereby interconnected.

39 Claims, 6 Drawing Sheets

US 7,108,714 B1

EXPANDABLE INTRALUMINAL ENDOPROSTHESIS

This application is a continuation of application Ser. No. 09/094,402 filed on Jun. 10, 1998 (now U.S. Pat. No. 6,117,165).

The present invention relates to an expandable intraluminal endoprosthesis comprising a tubular member having a first and second end and a wall surface disposed between said first and second end, the wall having a substantially uniform thickness and having a first diameter in a first, unexpanded state which permits intraluminal delivery of the member into a lumen of a body passageway, particularly a blood vessel, which member is capable of acquiring a second diameter in an expanded and deformed state upon the application from the interior of the tubular member of a radially outwardly extending force, which second diameter is variable and dependent on the amount of said force applied to the tubular member, whereby the tubular member may be expanded and deformed to expand the lumen of the body passageway. More particularly the invention relates to an expandable intraluminal vascular endoprosthesis which is especially useful for repairing or reconstructing blood vessels narrowed or occluded by a disease. Commonly this kind of medical device is referred to as vascular stent or graft.

Stents are prosthetic devices which are implanted inside a lumen in order to provide support for its wall and to assure an undisturbed flow through the lumen. This is particularly important in the field of angioplasty which is concerned with the repair and reconstruction of blood vessels. In that particular field stents are implanted within the vascular system to reinforce collapsing, partially occluded, weakened, or abnormally dilated sections of blood vessels. More generally, however, stents can be used inside the lumen of any physiological conduit or duct including the arteries, veins, bile ducts, the urinary tract, alimentary tracts, the tracheobronchial tree, a cerebral aqueduct and the genitourinary system. Moreover stents can be used inside lumina of animals besides humans.

Generally two types of stents may be distinguished. First there are self-expandable stents which automatically expand once they are released to assume a permanent deployed, expanded state. These stents expand to a defined diameter and are unable to remodel the true vascular anatomy over lengths greater than 2 cm. Their drawback is that the physician needs to place the right device and thereby has to rely on information derived from fluoro and angiographic equipment. A second type of stents concerns the so-called balloon expandable stents which generally involve a tubular member capable of receiving a balloon of a balloon-tipped catheter by means of which it may be deployed. The present invention particularly pertains to this second kind of stents.

A common procedure for implanting a balloon-expandable stent in a blood vessel involves mounting the stent in its unexpanded, crimped state on a balloon-tip catheter of a suitable delivery system. The catheter is then slipped through an incision in the vessel wall and down the length of the vessel until it is positioned to bridge the diseased or narrowed portion of the vessel. The stent is then expanded with the aid of the balloon-catheter against the internal wall of the vessel. This may be done after the vessel has been predilated and it has been determined that a stent is necessary. Alternatively the vessel could be dilated by the stent itself while the latter is expanded by means of the balloon. In both cases the stent will maintain its deployed, expanded form once the balloon is evacuated and the catheter retracted again in order to provide a permanent support for the blood vessel concerned.

A wide overview of vascular stents which are nowadays available is given in the Handbook of Coronary Stents by Patrick W. Serruys et al. of the Rotterdam Thoraxcentre Interventional Cardiology Group. This overview describes at page 21 ff, the so called Palmaz-Schatz™ stent as the gold standard in the field of stents. This stent concerns a number of consecutive slotted tubes of stainless steel which are mutually connected by means of one or more bridges. Although this stent is most widely used and tested in practice, it has been implanted in over 600000 patients all over the world, it still suffers from a number of drawbacks. The main drawbacks have to do with the stent-to-vessel-ratio uniformity and crimped as well as deployed flexibility. The stent-to-vessel-ratio involves the degree to which the vessel is supported by the stent in its expanded state and should not only be high, but preferably also uniform throughout the length of the stent. However, due to the inevitable bridges between adjacent tubes of the Palmaz-Schatz™ stent, there will be a bare area between adjacent segments of the stent once it has been deployed giving rise to a decreased and even poor stent-to-vessel-ratio at these locations. The other drawback concerns the rather high rigidity of the stent segments in their crimped and deployed state. As a consequence the stent has only a limited flexibility which hinders the delivery of the stent to its intended position inside the body. The poor deployed flexibility of this stent gives rise to a straightening of the vessel over segments longer than typically 2 cm which appears to be a primary cause for late term restenosis of the stented area. Typically this occurs after about 6 months after surgical post procedural.

A balloon expandable stent with a highly uniform stent-to-vessel ratio as well as an excellent flexibility in its crimped state is described at page 63 ff, of the same reference and concerns the Cordis Coronary Stent. This device is composed of a single piece of tantalum (Ta) wire. The wire is wrapped to form a continuous sine wave and helically wound along a longitudinal axis. Both ends of the wire are weld terminated. A similar device was presented at the annual symposium of the Radiological Society of North America (RSNA) 11/95. This peripheral stent embodiment incorporates intermediate welds, patterned through the length of the stent. This device contains adjacent helical turns of the wire which are welded together at adjoining locations and exhibits a highly regular distribution of the wire along the length of the device. Its properties, such as crimped profile and stent-to-vessel ratio, are uniform over its length both in the crimped and deployed states. However, because of its constitution this device offers only a poor design freedom when it conies to tailoring the design to add specific functionality and remove certain drawbacks. Also the internal stress in the device once it has been wound hinders the provision of reliable welds between adjacent turns. These welds as well as those to the ends of the wire moreover remain a weak point especially during expansion of the device.

SUMMARY OF THE INVENTION

It is an aim of the present invention to provide a balloon expandable stent which combines a high degree of uniformity and flexibility with excellent design capabilities.

To this end an expandable intraluminal endoprosthesis of the kind described in the opening paragraph according to the invention is characterized in that at least in said first unexpanded state at least a part of said wall of said tubular member comprises a substantially continuous structure of mutually staggered undulations which has been separated from a tube wall, in that said substantially continuous structure comprises at least one pattern which advances substantially helically along a longitudinal axis of said tubular body and in that said structure comprises connection elements connecting adjacent undulations, which connection elements are an integral extension of the undulations which they connected.

The structure making up the wall of the tubular member may be separated from a hollow tube by means of for instance laser cutting or a similar technique available to a skilled person. In this manner a substantially stress-free structure may be created incorporating a substantially helically advancing pattern which can be highly uniform and flexible throughout the length of the device but still facilitates unimpaired design freedom to tailor the pattern to meet additional functionality and to remove specific drawbacks. Moreover as the connecting elements are likewise separated from the tube as the rest of the structure and consequently are entirely integral with said structure the drawbacks associated with the welds in the prior art device may be avoided. The substantial helical pattern within the structure may be designed to form, upon deployment, a substantially continuously advancing spine as a kind of backbone of the device.

A specific embodiment of the endoprosthesis according to the invention is characterized in that said structure comprises a continuous filament which is separated from a tube wall, in that said adjacent undulations are staggered in a substantially helical configuration advancing along a longitudinal axis of the tubular body to form one of said at least one substantially helical pattern within said structure, and in that a first helical turn of said filament around said longitudinal axis of said tubular member is connected to an adjacent second such turn of said filament by means of at least one of said connection elements, being an integral extension of said filament. This embodiment to a large extent compares to the Cordis Coronary Stent referred to above, without however sharing the above described drawbacks of that device.

In order to improve on flexibility in a compressed as well as in a deployed state of the device a further specific embodiment of the endoprosthesis is according to the invention characterized in that adjacent turns of said filament are connected to one another by means of a number of connection elements less than the number of undulations in said turns. Due to the fairly unlimited design freedom in the device of the invention, the number of interconnections between adjacent turns may be adapted freely to suit the flexibility of the device. The less connection between adjacent turns, the more flexible the device will be. Said design freedom moreover allows a variation of the number of interconnections between adjacent turns within the same device to suit an optimal behaviour.

In a preferred embodiment an endoprosthesis is according to the invention characterized in that said structure comprises a number of turns of said filament whereby the connection elements to subsequent turns are radially shifted to form at least one further substantially helical pattern of said at least one substantial helical pattern within said structure. In this manner a kind of primary framework structure may be obtained which supports the vessel wall while maintaining deployed flexibility. More specifically a preferred embodiment of the endoprosthesis according to the invention is characterized in that at least a portion of the structure comprises a number of connection elements which are substantially equally divided in each turn of said filament and in that connection elements in successive turns are helically shifted by approximately one undulation pitch distance. By shifting the connection elements substantially a full pitch distance a structure is realized in which successive connection elements are linked to each other by substantially a full undulation of said first pattern. This undulation introduces significant slack and expandable diameter within the helical spine created by the interlinked connection elements which allows a very gradual expansion of the device transverse to its longitudinal direction. This reduces so-called foreshortening which is a longitudinal shrinking of the device as it is expanded and would otherwise limit the effective range of the device.

A further specific embodiment of the device according to the invention is characterized in that at least some of the connection elements comprise a strut diagonally interconnecting a first side of a first adjoining undulation to an opposite side of a second adjoining undulation, the strut being entirely integral with said adjoining undulations and having a direction different to the helical direction of said one substantial helical pattern within said structure. Upon deployment, this structure, will create a kind of spine which runs over a series of connection elements in a different, or even contra, helical direction compared to that of said one substantially helical pattern. Such multiple-helix structure is capable of providing a significant hoop strength whilst still being flexible and conformal to the natural vessel wall.

In a still further embodiment an endoprosthesis is according to the invention characterized in that the connection elements to subsequent turns are radially shifted by approximately one undulation pitch distance. Due to this regular pattern of connection elements one or more continuous, helically turning spines will be obtained in the deployed state of the device, formed by subsequent struts and the respective sides of the undulations they interconnect. These spines may form a scaffolding lattice which uniformly supports the vessel wall while maintaining deployed flexibility in order to be as conformal as possible with the natural form of the vessel concerned. It has been found that especially lack of the latter, resulting in unnatural straightening of the vessel over a certain length, is a primary cause for late term restenosis of the stented segment. Due to the deployed flexibility and its highly conformal deployed shape this still further embodiment of the invention aims to avoid this problem.

To further improve on flexibility while maintaining hoop strength, i.e. the ability to withstand inwardly directed radial forces, a further specific embodiment of the endoprosthesis according to the invention is characterized in that the first side of said first undulation, said opposite side of said second undulation and said strut have a first filament width and in that the opposite side of said first undulation and the first side of the second undulation have a second filament width, the first filament width being larger than the second filament width. The inventor has recognized that said second filament width may be made smaller than said first filament width, thus gaining flexibility, without deteriorating the strength of the device and particularly its radial hoop strength.

In a further specific embodiment the endoprosthesis according to the invention is characterized in that said strut connecting opposite sides of adjoining undulations of subsequent turns have a substantially S-shaped structure. Such a double curved structure of the connection elements creates more slack between mutually interconnected undulations allowing more expansion as well as an improved stent to vessel ratio at said area once the prosthesis has been deployed.

A still further preferred embodiment of the endoprosthesis according to the invention is characterized in that the connection elements each comprise two intersecting struts which are entirely integral with each other and with the adjoining undulations which they connect. The inventor has recognized that on deployment of the device such an interconnection element will first rotate around its central axis before the entire force applied pulls axially on the point of intersection. As a consequence a certain stress relief is incorporated in the device which allows for a smaller filament width. This does not only add to the flexibility of the device but also leads to a more favourable radio-opacity. Moreover, the intersecting struts leave a substantially unchanged scaffolding area or footprint upon deployment of the structure thereby improving on the eventual stent-to-vessel ratio of the device compared to a connection element which will almost entirely stretch upon deployment.

The design freedom gained by the endoprosthesis according to the invention appears fairly unlimited and can be applied to precisely tailor the properties of the device to specific requirements. Not only the form, number and the location of connection elements but also the filament width and form of particular parts may be adapted in this sense. As an example, a further specific embodiment of the invention is characterized in that the undulations in said filament have a first mutual pitch in a first of said turns of said filament and a second mutual pitch in a second of said turns, the first and second pitch being different from each other. Varying the mutual pitch of the undulations will generally give rise to more or less flexibility in combination with less or more vessel support at the zones concerned.

A still further embodiment of the endoprosthesis according to the invention is characterized in that at least a part of at least one undulation in at least one turn of said at least one substantially helical pattern has an increased amplitude, while at least the adjoining part of an adjoining undulation in an adjacent turn has a correspondingly decreased amplitude. In this case the mechanical properties of the device and especially the manner of deployment as well as the stent-to-vessel ratio may be tailored by offsetting the point where adjacent undulations meet.

More specifically a further embodiment of the endoprosthesis according to the invention is characterized in that a first pair of adjacent undulations of said structure is connected by means of a first connection element, in that a second pair of adjacent undulation of said structure is connected by means of a second connection element, in that in between said first and second pair of connection elements at least one undulation of an intermediate pair of undulations has an increased amplitude, to bridge at least part of the length of said first and second connection element. In this case the inevitable length of the connection elements between adjacent turns of the device is at least partly compensated by the increased amplitude of said at least one undulation, leading to a more uniform deployed stent-to-vessel ratio.

Besides, or even instead of, being formed by a series of substantially helically staggered undulations, a substantially helically advancing pattern within the structure may also be created by the connection elements in themselves. In this respect, a specific embodiment of the endoprosthesis according to the invention is characterized in that said structure comprises at least one series of connection elements which are substantially regularly distributed over at least part of the length of said tubular body and in that successive connection elements within said at least one series are radially shifted to form one substantially helical pattern within said structure. More specifically, a preferred embodiment of the endoprosthesis according to the invention is characterized in that said successive connection elements are mutually connected by an elongated member which has a greater length than the linear distance between said connection elements in said first unexpanded state of the structure, in order to impart radial expandability to the structure.

In this manner a helically advancing spine is realised throughout at least a part of the device which adds to the scaffolding lattice of the structure, especially in the deployed state of the device. One or even more of such spines may give the device a considerable hoop-strength and supporting capability, without depriving the structure of its crimped as well as deployed flexibility. The greater length of the elongated member adds expandable diameter to the individually connected connection elements, imparting additional slack within the structure, an improved expandability and less fore-shortening on the device. This additional circumference allows for side branch access greater than the maximum expanded diameter of the stent along the longitudinal axis. In this respect, a specific embodiment of the endoprosthesis according to the invention is characterized in that said elongated member comprises a substantially S-curved bent. The S-curved members are situated along the spiral helix equidistantly spaced, along the longitudinal axis of the tubular body, and primarily allow the device to uniformly expand out radially enabling the structure to orient itself into a helical structure upon deployment. In a more particular embodiment the S-curved bent is orientated substantially parallel to the longitudinal axis of the tubular body, which allows the member to uniformly expand perpendicular to said axis. This prevents the device from twisting and rotating on the balloon-catheter, or the like, as the device undergoes expansion.

The endoprosthesis according to the invention may have a uniform structure throughout the device. A preferred embodiment of the device is however characterized in that the tubular body comprises a central portion, two outer portions at opposite ends of said tubular body and at least one intermediate portion in between the central portion and each of said end portions, the different portions being designed according to their specific function in the device. This embodiment is based on the recognition that different requirements may have to be imposed on different parts of the endoprosthesis to precisely meet the specific function or desired behaviour of the part concerned while the device is either unexpanded, expanded or in a transition between the unexpanded and expanded state. The present invention provides for a device in which this kind of tailoring may be implemented.

More particularly a further embodiment of the endoprosthesis according to the invention is characterized in that at least in one of the two outer portions of the tubular body the undulations in said structure have a gradually decreasing amplitude whether or not in combination with a changing pitch or filament width in order to render a free end of said portion substantially transverse to the longitudinal axis of said body, at least in said first unexpanded state of said structure. Such a square-like tubular end of the endoprosthesis prevents an undesired cantilever protrusion of the last turn which otherwise could harm the wall of the lumen while the device is being navigated to its intended position. Moreover this structure improves the mechanical bond between the endoprosthesis and the balloon of the catheter used to manipulate the device within the body. The square end is created by gradually decreasing the amplitude and changing the pitch of the last few undulations until there is a final smooth transition forming the desired square end. Modifications of the filament width at this area may further improve this part's behaviour.

A still further embodiment of the endoprosthesis according to the invention is characterized in that said central portion of the tubular body comprises a first number of connection elements per full helical turn of said at least one substantially helical pattern within said structure, in that at least one of said intermediate portions comprises a second number of connection elements of the structure per full helical turn of said at least one substantially helical pattern within said structure, and in that the first number of connection elements is smaller than said second number of connection elements imparting a difference in flexibility between both portions of the tubular body. More precisely, the central portion will exhibit more flexibility than the intermediate portions due to the lower number of interconnections between adjacent turns. To accommodate this difference within the structure, a specific embodiment of the endoprosthesis according to the invention is characterized in that the central portion and any one of said intermediate portions are separated from each other by a transitional portion in order to smoothly change the number of interconnections between adjacent turns from the first number to the second number of connection elements per full helical turn of said pattern.

In a more specific embodiment the endoprosthesis according to the invention is characterized in that adjacent turns in said central portion comprise a number of connection elements which are equally divided and in that connection elements in subsequent turns are helically shifted by approximately one undulation pitch distance. For example, there could be six adjoining helical segments with three equally spaced connection elements, situated approximately 120° with respect to one another or six opposing helical segments with two equally spaced connection elements situated approximately 180° with respect to one another. This specific design yields the most flexible structure in the central region, both crimped and deployed.

Once deployed, the structure will orient itself in line with the helical lattice structure which it forms, exhibiting three intertwining continuous lattice legs within the intermediate region and only two of those legs in the central region. The intermediate region will possess more stiffness in order to counteract the balloon expansion, known as the "dog bone effect", which causes the ends of the device to flare prematurely prior to the deployment of the central section and which results in an undue amount of foreshortening upon expansion. Moreover the intermediate regions serve as a relief between the end portions and the central region of the device.

BRIEF DESCRIPTION OF THE DRAWINGS

The present invention will now be further described in more detail with reference to the following figures in which like elements are provided with the same reference numerals.

The figures are drawn merely schematically and not to scale. More particularly some dimensions may be exaggerated to more clearly point out one or more aspects of the present invention. Like parts the drawings are indicated as much as possible by like reference signs.

DESCRIPTION OF THE PREFERRED EMBODIMENTS

Figure 1:
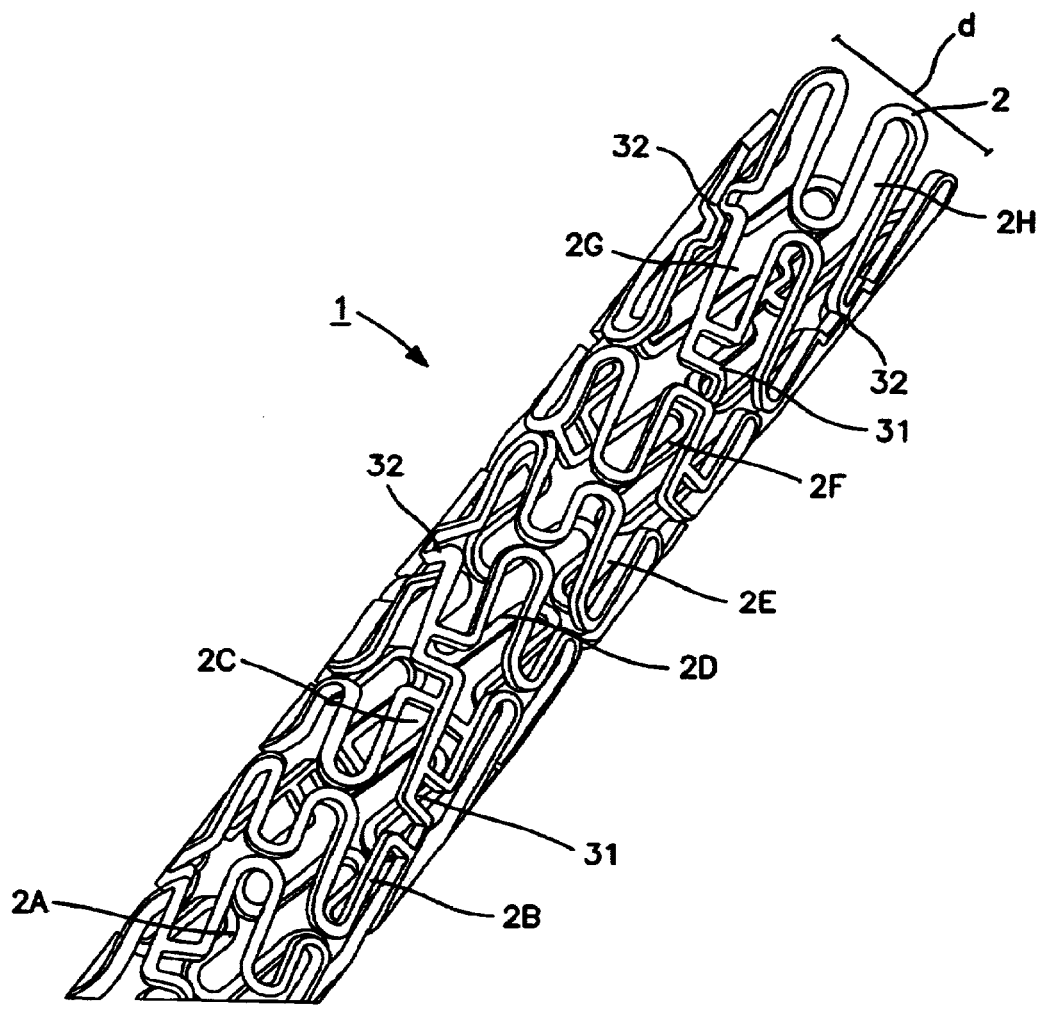
FIG. 1 shows an isometric view of an embodiment of an expandable intraluminal endoprosthesis in accordance with the present invention.

FIG. 1 gives an isometric view of an expandable intraluminal endoprosthesis according to a specific embodiment of the present invention. The endoprosthesis, hereinafter briefly referred to as stent, comprises a tubular member 1 which has been separated out of a tubular body of a suitable bio-compatible material. As such for instance high grade stainless steel (SST), a nickel-titanium based alloy referred to as Nitinol (NiTi), several cobalt based alloys and a Niobium-Titanium (NbTi) based alloy qualify. In this case the latter material may be chosen because of its excellent mechanical strength, corrosion resistance and radiopaque fluoroscopic signature. In the first, unexplained state shown, the tubular member 1 is drawn with a first diameter d which permits delivery of the member into a lumen of a body passageway, particularly a blood vessel. The member 1 is capable of acquiring a second, expanded and deformed diameter upon the application of a radially outwardly extending force from its interior, usually by means of a balloon-catheter. This second diameter is variable and dependent on the amount of force applied. Inevitably the member will show a certain amount of recoil which means that the device will retract more or less after the balloon has been evacuated. Accordingly the second diameter will be slightly smaller than the diameter to which the stent has been expanded. Nevertheless the tubular member may be expanded and deformed to expand the lumen of the body passageway to again assure an undisturbed flow through the lumen, like a blood vessel.

The wall of the stent comprises a substantially continuous structure which in this example consists of a continuous filament which has been cut out from the tube wall in a substantially helical fashion with a width between about 0.10 and 0.17 mm. This may be done by means of laser cutting, electrochemical etching, electromechanical discharge or any other suitable technique preferably followed by a suitable surface treatment, like etching to deburr and or round off possible sharp edges. In this example a tubular body with an internal diameter of about 3.0 mm, a wall thickness of about 1.0 mm and a length of about 30 mm has been chosen as a starting material. However, other dimensions are likewise feasible within the scope of the present invention. Particularly the length may be adapted to the diseased part of the lumen to be stented in order to avoid the necessity of separate stents to cover the total area. The filament-structure comprises a number of undulations 2 which are mutually staggered in helical pattern advancing around a central longitudinal axis of the device. In order to retain a coherent body subsequent turns 2A–2H of the filament are interconnected by means of one or more connection elements 31,32 which are entirely integral with the undulations thereby connected, as they are cut altogether from one and the same tubular body. To retain flexibility, both unexpanded as well as deployed, the number of connection elements per helical turn is less than the number of undulations in said turn. This is further elucidated in FIG. 2 which gives plan view of the device as if it were cut open. As emerges quite clearly from this figure, the connection elements 31 to subsequent turns are radially shifted by about half undulation pitch distance ½L to form a helical pattern X—X, Y—Y. Once deployed, these patterns will expand to a helically turning spines which form a primary framework or scaffolding lattice of the deployed stent. This framework supports the vessel wall highly uniformly throughout the device and moreover is capable of withstanding substantial inwardly directed radial forces. This capability of the framework is referred to as its hoop strength.

Figure 2:
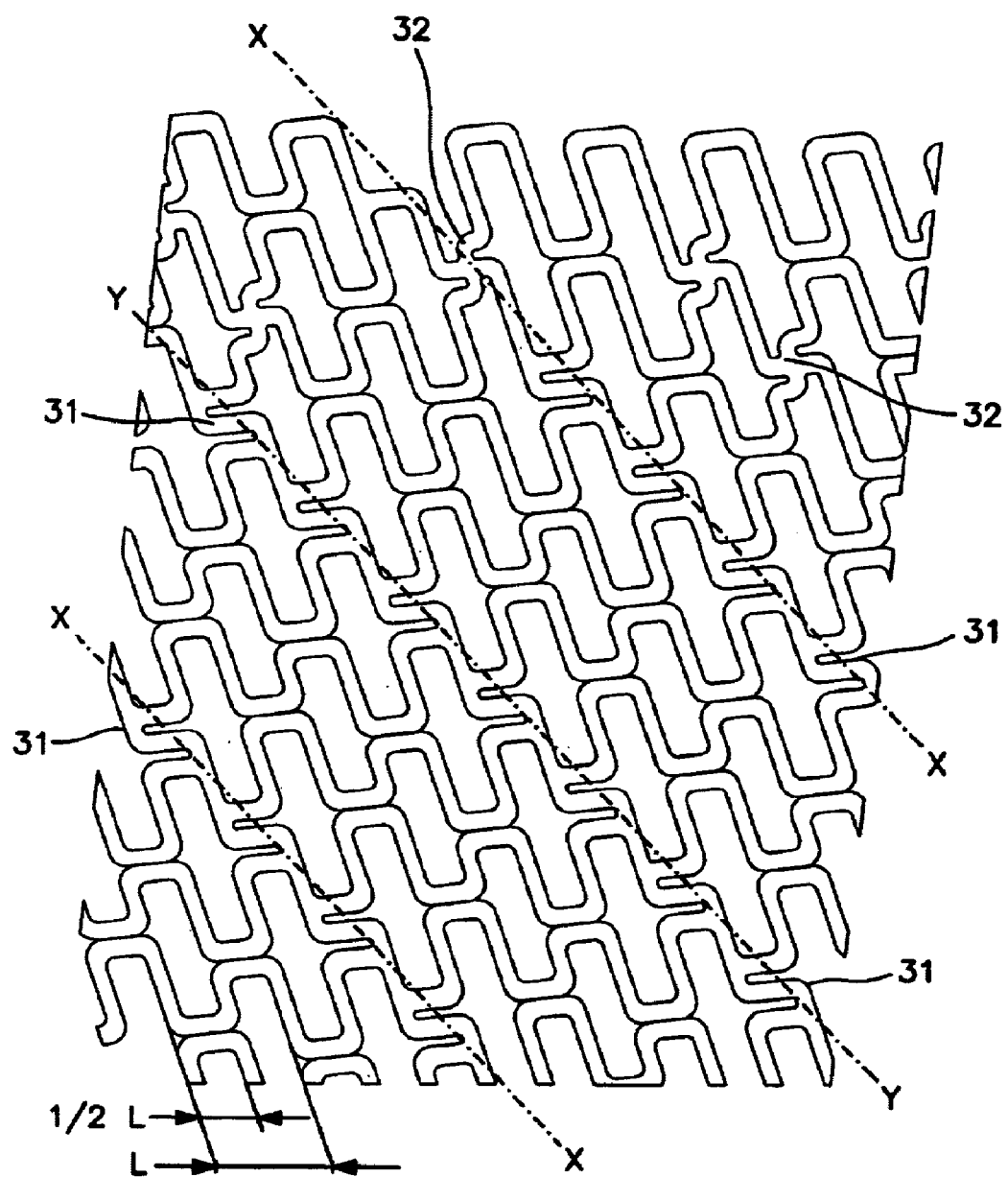
FIG. 2 is a plan view of the endoprosthesis of FIG. 1.

The lower drawing part of FIG. 2 shows a part of a central modular portion of the device in which successive turns of the filament are interconnected by means of only two connection elements 31, which are shifted about 180° with respect to one another, while the upper part shows an end portion of the device together with an intermediate portion in which three equally spaced connection elements 31,32 interconnect adjacent undulations from successive turns of the filament with each other. As a result the parent scaffolding lattice of the deployed device will be composed of only one helically advancing spine within the central region and will comprise two helically revolving spines within the other regions. Although the latter provides less flexibility, it leads to an improved adhesion to the balloon-catheter by which the device is guided through the lumen and moreover counteracts a so-called dog bone effect, which is a premature expansion at the tail ends of the device. The central portion of the device, i.e. the lower drawing part, one the other hand retains maximum flexibility and conformability due to the smaller number of interconnections between adjacent undulations within this segment.

In this example two kinds of connection element are used, denoted 31 and 32 respectively. Both types of connection elements feature a strut 3 which is S-shaped and diagonally interconnects opposite sides of adjacent undulations from successive turns of the filament in a helical direction different to that of the staggered undulations themselves, see also FIG. 3E. These struts will be referred to as major struts as they are part of the lattice spines described hereinbefore. The struts will be referred to as major struts as they are part of the lattice spines described hereinbefore. The second type of interconnection element 32 moreover features a second, S-shaped diagonal 4 strut intersecting the first one, see also FIG. 3D. Due to this shape an interconnection element of the second kind 32 will first start to rotate around its central axis once the stent is being deployed with only a limited force being exerted axially in the diagonal 3 of the connection element. Only after the first diagonal 3 has become fully in line with the sides of the undulations it interconnects, does it have to withstand the entire force axially. This incorporated slack and stress relief allows thinner strut width and filament width over the lattice legs which can be useful for decreasing the radio-opacity at this area as well as improves its unexpanded, crimped as well as deployed, expanded flexibility. Moreover the support area covered by a connection elements of this second kind will not decrease much upon deployment of the device. As a result a larger "scaffolding footprint" will remain after deployment compared to any of the other types of connection elements shown which all will stretch substantially upon deployment leaving only the thin major strut 3 as "scaffolding footprint".

Besides the types connection elements depicted in the drawing also other shapes are feasible, as the invention imposes hardly no limitation of the design of any part of the device including the shape of the interconnections used. Examples of other shapes which could advantageously be used in a device according to the invention are shown in FIGS. 3A–3G. The connection elements of FIGS. 3A–3C merely comprise a straight strut 3 connection adjacent undulations, whereas the main strut 3 of the connection elements shown in FIGS. 3D–3F have a clearly S-curved shape. This shape introduces more slack and expandability in the structure. The longer this segment, the more slack and expandability there is in the structure and especially in the spinal ladder created by these connection elements in the eventual deployed device. A simple formula can be derived from the expanded state, defining the relative increase of the strut length and the effect it has on the expansion range of the device.

Figure 3:
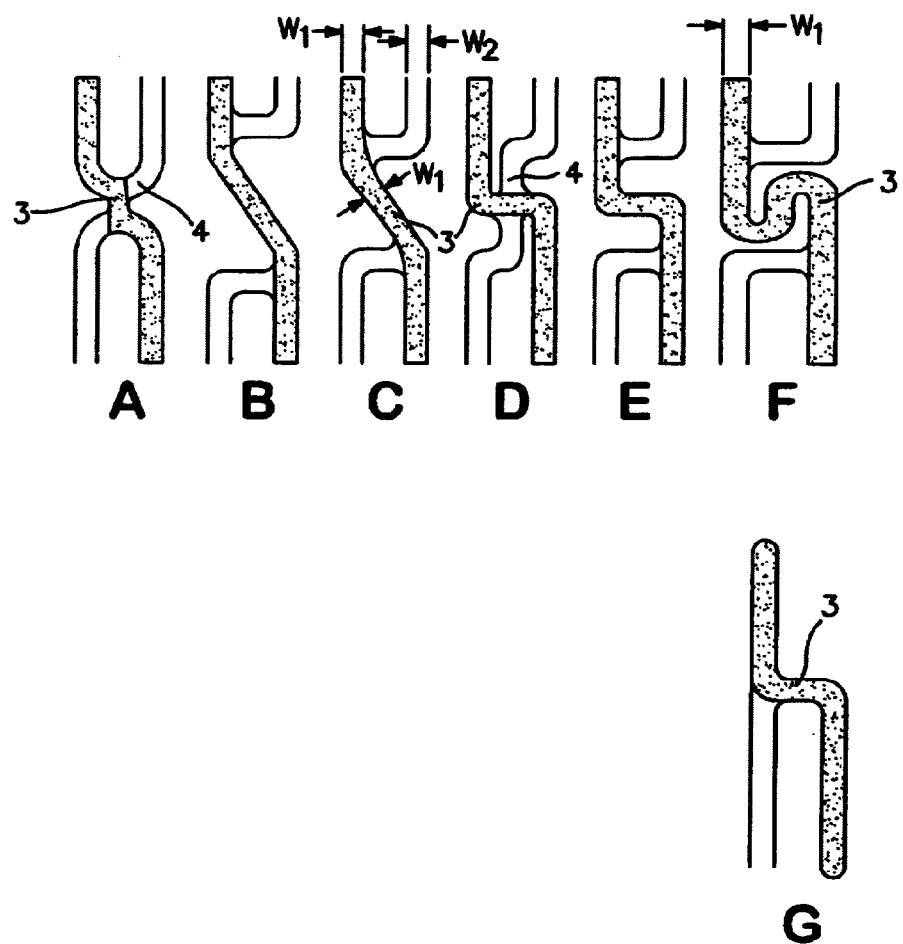
FIG. 3 shows alternative embodiments of interconnection elements to be in a device according to the invention.

The major strut 3, i.e. the strut eventually forming part of the parent scaffold or framework of the device once it is deployed, is indicated in FIG. 3 by a dotted hatch. In a special embodiment this strut as well as the undulation sides which it interconnects are given a first filament width $w_1$ sufficiently large to withstand the axial forces imposed thereon during expansion of the device, whilst the other undulation sides and if applicable the other strut of the connection element are given a second filament width $w_2$, at least locally, to gain flexibility and decrease radio-opacity. Specifically the filament width is modified in the central portion of the device to improve its overall flexibility such that a first filament width $w_1$ of approximately 0.14 mm is taken whereas the second filament width $w_1$ is reduced to about 0.11 mm.

In order to avoid a substantial disruption of the stent to vessel support by pairs of undulations from successive turns of the filament which are not mutually interconnected by a connection element, the amplitudes of the undulations within such pair may be adapted to fill the gap which would otherwise remain due to the inevitable length of a connection element elsewhere in the structure. This is for instance apparent from FIG. 2 where all adjacent peaks and valleys of pairs of undulations out of successive turns which are not interconnected nevertheless adjoin one another. This is a result of the adapting the amplitude of at least one of the undulations within such pair of undulations. This can imply that both, the peak and the valley have an increased amplitude, that only one of those parts is enlarged, the other part remaining unchanged, or even that either the peak or the valley has a increased amplitude while the other part has a decreased amplitude. Also in this respect, the designer has full freedom to tailor the stent design to allow optimal behaviour of the stent in its unexpanded state, expanded and/or transitional state.

Figure 4:
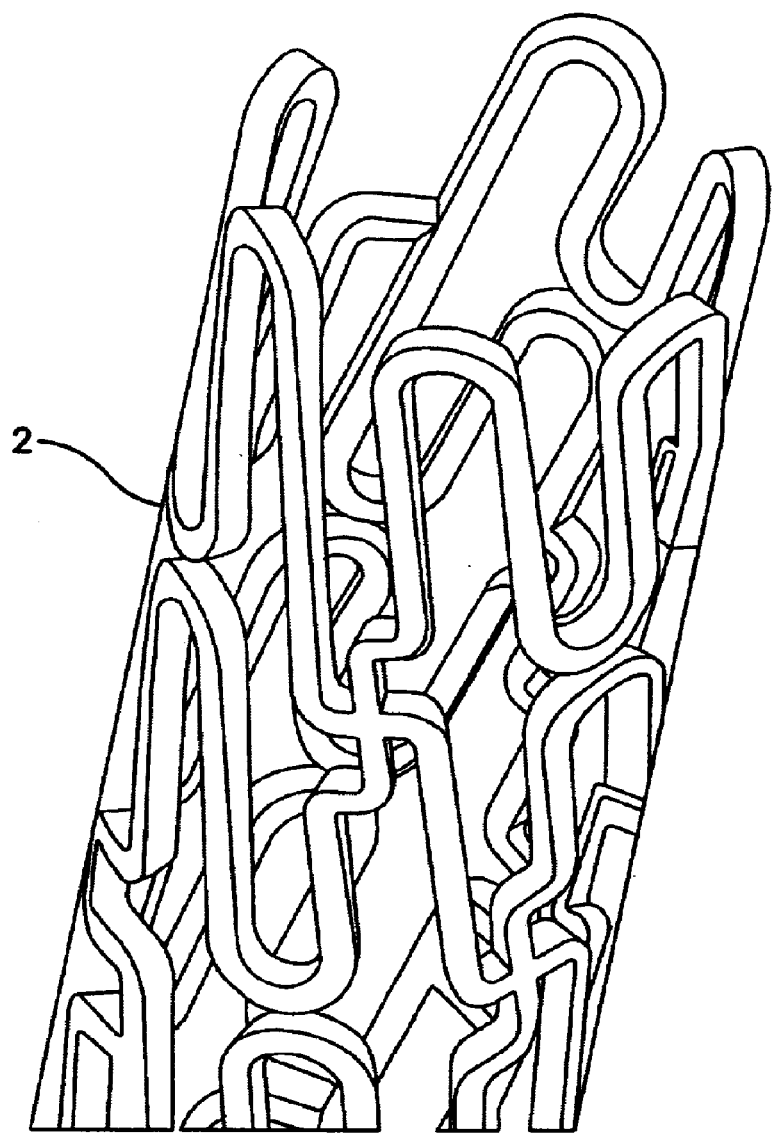
FIG. 4 is an enlarged view of an end portion of the endoprosthesis of FIG. 1.

The end portion of the device ends substantially transverse to the central axis of the device in order to avoid a cantilever usually associated with a helix shape which could otherwise harm the wall of the lumen through which the stent is navigated. This end portion is shown in more detail in FIG. 4. Its particular shape is obtained by gradually decreasing the amplitude in the last few undulations and adapting their mutual pitch. Due to the invention this may be done without introducing any stress in the device as the filament is simply cut in the desired pattern. The deviating amplitudes and mutual pitch are best recognized from the plan view of FIG. 2. The end modules exhibit a greater stent-to-vessel ratio than the central and intermediate portions due to the increased metal-to-surface-area in the expanded configuration. The more complex structure of the end portions moreover give rise to a greater amount of foreshortening upon expansion, thus producing a more dense pattern yielding additional stent-to-vessel ratio.

Figure 5:
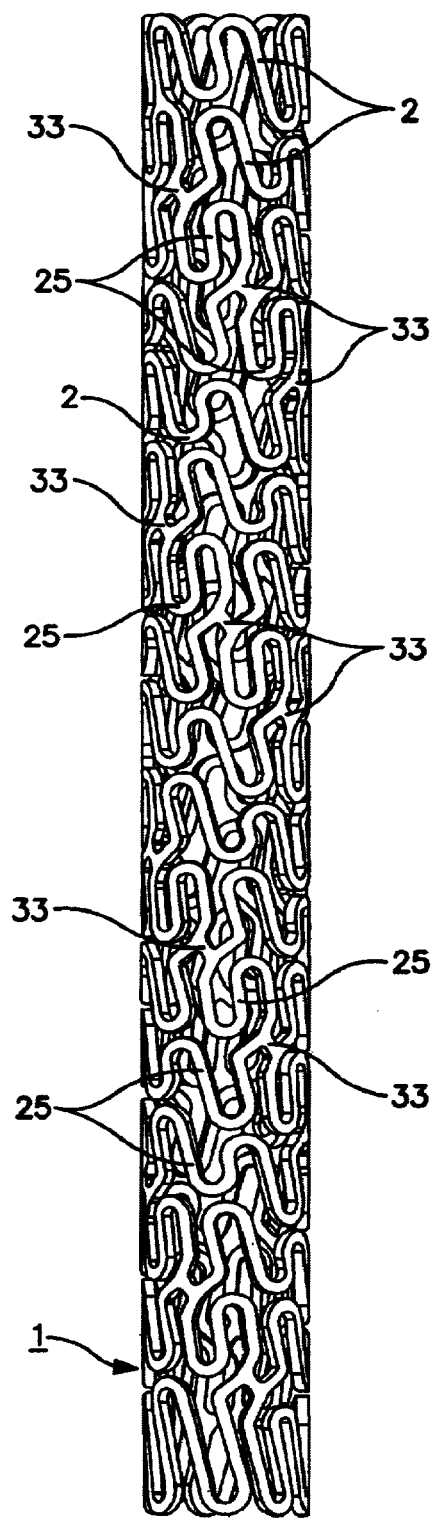
FIG. 5 shows an isometric view of a second embodiment of an expandable intraluminal endoprosthesis in accordance with the present invention.
Figure 6:
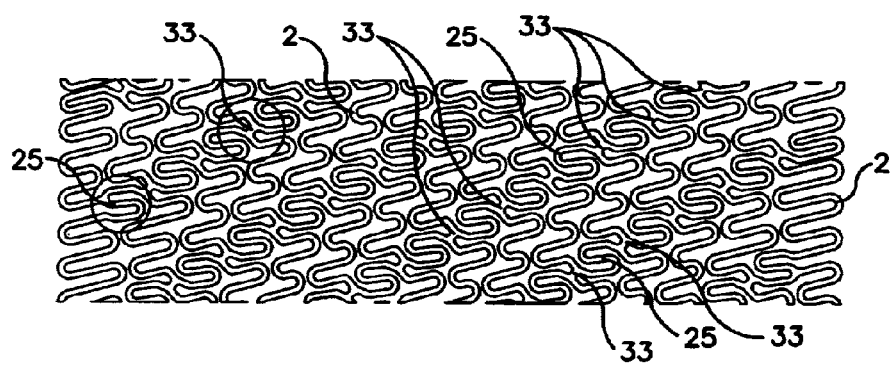
FIG. 6 shows a plan view of the device of FIG. 5 in a unexpanded state.
Figure 7:
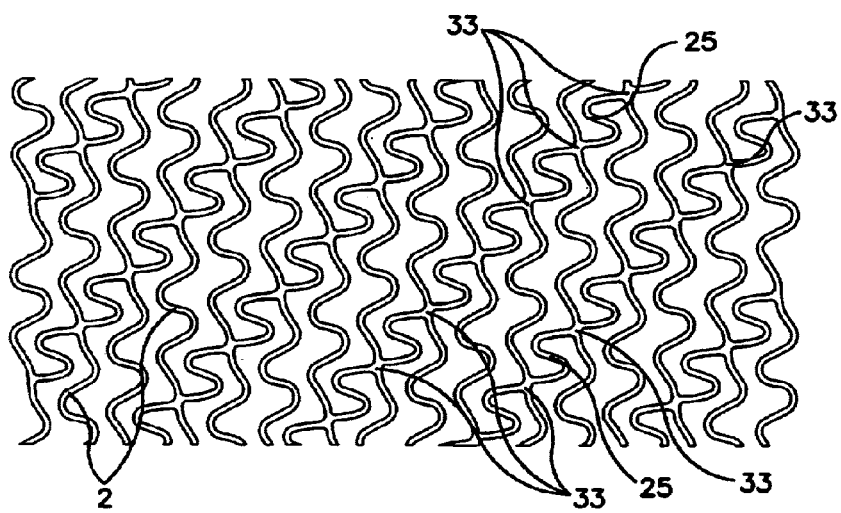
FIG. 7 is a plan view of the device of FIG. 5 in a expanded, deployed state.

A second embodiment of the device according to the invention is depicted in FIGS. 5–7. This device comprises a tubular body 1 and has been manufactured using similar techniques as in the first embodiment, although in this case a more complicated structure has been created consisting of more than just a single, wrapped filament. However, like in the first embodiment, the structure of the device is composed of a substantially helical pattern of mutually staggered undulations 2, with connection elements 33 interconnecting some undulations from successive turns of said pattern. The connection elements within this structure primarily comprise two intersecting struts like the type reflected in FIG. 3D.

Different to the structure of the first embodiment, connection elements 33 to subsequent turns of said pattern are shifted by about a full pitch distance. As a result a full undulation 25 will link said connection elements 33 to one another and as such creates an elongated member 25 in between the connection elements 33. Said elongated member formed by an intermediate undulation comprises a S-curved bent and is longer than the linear distance between the interconnection elements thereby linked to each other, at least in the crimped state shown in FIGS. 5 and 6. This imparts additional slack and considerable expandability to the spinal ladders which are formed by such a series of linked connection elements in the deployed state shown in FIG. 7. Moreover the orientation of the S-curved bents in said elongated members 25, which is substantially parallel to the longitudinal axis of the body at least in the crimped state shown in FIGS. 5 and 6, allows the member 25 to uniformly expand in a direction which is substantially perpendicular to said axis. This prevents the device from twisting and turning on the balloon-catheter once it is being expanded.

Like in the first embodiment, also in this case said series of interlinked connection elements mutually shifted by a pitch distance, form further substantially helically advancing patterns within the structure. Like the staggered undulations themselves, these further helically revolving patterns will mature to helical spines running through the structure once it is being expanded, see FIG. 7. These additional spines however run in a different direction than the spines created by the undulations, indicated by the straight lines in FIG. 7, which results in an eventual structure with a considerable hoop strength in combination with an excellent unexpanded and deployed flexibility. As the device of the invention allows for a very large design freedom, these aspects may be once more tailored throughout the device to fit the best overall characteristics in each portion of the device.

Although the invention has been described hereinbefore with reference to merely a few embodiments, it will be appreciated that the invention is far more wide spread applicable. Within the scope of the invention many other embodiments and variations are feasible for a skilled practitioner. As such he may vary for instance the mutual pitch of a few or more subsequent undulation with or without a variation of the amplitude in order to tailor the stent-to-vessel ratio and flexibility at the area concerned. Also, additional modular portions individually recognizable in the stent could be implemented in the stent in order to add specific functionality. As such, a transitional portion might be interposed between the relatively flexible central portion and the more stiff intermediate and end portion in order to alleviate the structural transition between those parts of the stent. Also the number of connection elements within a full turn of the helical pattern may be raised to introduce additional lattice spines to the deployed device, resulting in even a larger hoop strength and supporting capability of the device.

Likewise, the filament width as well undulation shapes may be varied and adapted to suit specific required characteristics besides the flexibility and stent-to-vessel ratio. For instance, the foreshortening of the device, i.e. the amount of length reduction upon expansion from the crimped to the deployed state of the device, its degree of recoil, its hoop strength as well as it radio-opacity may be so varied and adapted. In any event the present invention provides the designer with the greatest amount of freedom conceivable.

Also the elongated members interlinking a series of connections elements like in the second embodiment need not coincide with undulations of the pattern and can be introduced in the structure as separate elements. These members moreover need not necessarily comprise a full S-curved bent or even any S-curved bent at all and may on the other hand consist of more than just one such bent. Also in this respect the designer has total freedom to tailor the device to his demands.

What is claimed is:

1. A stent comprising:
a first square-like tubular end;
a second square-like tubular end;
a main body located between the first and second ends, the main body having a length L, a longitudinal axis, a first diameter for allowing the stent to be introduced into a vessel and a second expanded diameter, the main body comprised of:
a plurality of contiguous filaments arranged to form: (i) a first segment propagating helically with respect to the longitudinal axis of the main body of the stent, the first segment having a repetitious pattern that comprises peaks and valleys and (ii) a second segment, the second segment also having a repetitious pattern and propagating helically with respect to the longitudinal axis of the main body; and
wherein the first and second segments are joined together by radially expandable connecting bridges that are integral portions of the first and second segments and wherein the segments cross each other.

2. The stent of claim 1, wherein the first and second segments have different pitches.

3. The stent of claim 1, wherein the pattern of the first segment is distinct from the pattern of the second segment.

4. The stent of claim 1, wherein the stent is manufactured from a self-expanding material.

5. The stent of claim 1, wherein the stent is manufactured from a plastically deformable material.

6. The stent of claim 1, wherein the first and second segments have a circumferential dimension that is parallel to the circumference of the stent.

7. The stent of claim 6, wherein:
the first and second segments each have a helical length; and
the first and second segments also each have a total filament length that is longer than the length L of the main body.

8. The stent of claim 1, wherein the stent is manufactured from a tube by removing material to form the plurality of contiguous filaments.

9. The stent of claim 8, wherein a laser is used to remove the material.

10. The stent of claim 1, wherein the repetitious pattern of at least one of the segments has an amplitude that varies.

11. The stent of claim 10, wherein the repetitious pattern is generally sinusoidal.

12. A stent having an overall length L and comprising two end sections and a generally cylindrical shaped body disposed between the end sections, the body comprised of:
   a plurality of contiguous filament segments forming a first repetitious pattern and propagating generally helically through the body, the first repetitious pattern having a first pitch; and
   a plurality of radially expandable connecting bridges longitudinally joining one portion of the first repetitious pattern with a second portion of the first pattern, the connecting bridges, along with portions of the first pattern forming a second repeating pattern that propagates helically through the body and has a second pitch that is less than the first pitch and wherein the connecting bridges are integral portions of the first and second patterns.

13. The stent of claim 12, wherein the first and second patterns begin at one end section and terminate at the second end section.

14. The stent of claim 12, wherein the first and second patterns have a starting point distal of one end section and an ending point proximal of the other end section.

15. The stent of claim 12, wherein the first and second patterns each have a circumferential dimension and wherein the first and second patterns circumferentially expand when the stent is expanded.

16. The stent of claim 15, wherein: the length of the filament segments comprising the first repeating helical pattern is greater than the overall stent length L; and
   the length of the filament segments comprising the second repeating helical pattern is greater than the overall stent length L.

17. The stent of claim 16 having square-like tubular ends.

18. The stent of claim 16, further comprising a first end section having a length $L_{end1}$ and a second end section having a length $L_{end2}$, wherein L is greater than either $L_{end1}$ or $L_{end2}$ and $L_{end1}=L_{end2}$.

19. The stent of claim 18 having square-like tubular ends.

20. The stent of claim 15, wherein the first and second patterns have helical lengths $L_{hel1}$ and $L_{hel2}$, respectively and wherein the total filament length of the filament segments comprising the first pattern is greater than $L_{hel1}$ and the total filament length of the filament segments comprising the second filament pattern is greater than $L_{hel2}$.

21. The stent of claim 15, wherein at least one of the first or second repeating patterns comprises a repetitiously changing amplitude.

22. A stent consisting essentially of a generally tubular body having a proximal end and a distal end, the body having a substantially continuous structure consisting essentially of:
   a plurality of filament segments arranged to form a first repetitious pattern comprised of peaks and valleys and that advances substantially helically along the longitudinal axis of the stent;
   a plurality of radially expandable connecting bridges connecting proximal portions of the first helically advancing pattern to distal portions of the first helically advancing pattern, wherein the connecting bridges connect peaks to valleys; and
   wherein the connecting bridges and the peaks and valleys that they connect are comprised of a continuous piece of material.

23. The stent of claim 22, wherein at least some of the peaks and valleys are comprised of curvilinear filaments.

24. The stent of claim 23, wherein at least a portion of the first repetitious pattern is generally sinusoidal.

25. The stent of claim 22, wherein the connecting bridges are staggered to form a second repetitious helical pattern that is not parallel to the first pattern.

26. The stent of claim 25, wherein the connecting bridges forming the second pattern are not contiguous.

27. The stent of claim 25, wherein the first and second repetitious helical patterns have opposing pitches.

28. The stent of claim 27, wherein the first and second repetitious helical patterns share common filament segments.

29. The stent of claim 28, wherein the stent is manufactured from a cylindrical hollow tube.

30. A generally cylindrical shaped stent having a longitudinal axis, the stent, when oriented with its longitudinal axis in a vertical direction, comprising:
   (i) a first expandable element comprised of an undulating filament segment comprised of at least one peak and at least one valley having substantially the same widths;
   (ii) a second expandable element comprised of an undulating filament segment comprised of at least one peak and at least one valley having substantially the same width, the second expandable element located above and to the left of the first expandable element;
   (iii) a first connecting element connecting the first expandable element to the second expandable element, the first connecting element being located to the left of the at least one peak and the at least one valley of the first expandable element and not being connected directly to the at least one peak and the at least one valley of the first expandable element, and the first connecting element being located to the right of the at least one peak and the at least one valley of the second expandable element, and the first connecting element not being connected directly to the at least one peak and the at least one valley of the second expandable element;
   (iv) a third expandable element comprised of an undulating filament segment having at least one peak and at least one valley having substantially the same widths, the third expandable element located above and to the left of the second expandable element; and
   (v) a second connecting element connecting the second expandable element to the third expandable element, the second connecting element located to the left of the at least one peak and at least one valley of the second expandable element and not being connected directly to the at least one peak and at least one valley of the second expandable element, the second connecting element located to the right of the at least one peak and the at least one valley of the third expandable element and not connected directly to the at least one peak and the at least one valley of the third expandable element.

31. The stent of claim 30, wherein the first, second, and third expandable elements have substantially the same shapes.

32. The stent of claim 31, wherein the first, second, and third expandable elements have substantially the same sizes.

33. The stent of claim 30, further comprising a helical segment comprised of:
   the first, second, and third expandable elements; and
   the first and second connecting elements.

34. The stent of claim 33, wherein the first, second, and third expandable elements are each comprised of at least three distinct generally linear filament segments that are substantially parallel to the longitudinal axis of the stent.

35. The stent of claim 34, wherein:
the peaks of the expandable elements are connected directly to two of the three distinct generally linear filament segments and to no other filament segments; and
the valleys of expandable elements are connected directly to two of the three distinct generally linear filament segments and to no other filament segments.

36. A stent comprising:
a first end;
a second end;
a generally cylindrically shaped body disposed between the first and second ends, the body comprising:
a plurality of first helical segments, each helical segment comprised of:
a plurality of expandable elements, each expandable element comprised of:
a first filament portion;
a second filament portion;
a first valley portion connecting the first filament portion to the second filament portion;
a third filament portion;
a first peak portion connecting the second filament portion to the third filament portion; and
wherein the first valley portion and the first peak portion have the same approximate widths; and
a plurality of connecting elements connecting the first filament portion of one of the expandable elements to the third filament portion of another of the expandable elements.

37. The stent of claim 36, wherein the expandable elements have the same general shape.

38. The stent of claim 37, wherein the expandable elements have the same approximate size.

39. The stent of claim 38, further comprising a second filament segment comprised of an undulating portion having peaks and valleys, the second filament segment propagating helically and having an opposing pitch with a value different from that of the first helical segments.

* * * * *